US008734481B2

(12) United States Patent
O'Connell et al.

(10) Patent No.: US 8,734,481 B2
(45) Date of Patent: May 27, 2014

(54) REMOVEABLE FILTER HEAD (75) Inventors: Paul T. O'Connell, Evanston, IL (US); Guy Nadal, Poitiers (FR); Armelle Nadal, legal representative, Poitiers (FR)

(73) Assignee: B. Braun Medical SAS, Boulogne-Billancourt (FR)

( * ) Notice: Subject to any disclaimer, the term of this patent is extended or adjusted under 35 U.S.C. 154(b) by 1776 days.

(21) Appl. No.: 11/910,595

(22) PCT Filed: Apr. 4, 2006

(86) PCT No.: PCT/US2006/012453
§ 371 (c)(1),
(2), (4) Date: Sep. 6, 2010

(87) PCT Pub. No.: WO2006/107939
PCT Pub. Date: Oct. 12, 2006

(65) Prior Publication Data
US 2011/0106133 A1 May 5, 2011

Related U.S. Application Data (60) Provisional application No. 60/668,036, filed on Apr. 4, 2005.

(51) Int. Cl.
A61B 17/00 (2006.01)
(52) U.S. Cl.
USPC .......................................... 606/202
(58) Field of Classification Search
USPC ................................. 606/200, 202
See application file for complete search history.

(56) References Cited

U.S. PATENT DOCUMENTS

| 344,141 | A | 6/1886 | Shoults |
| 2,281,448 | A | 9/1941 | Mathey |
| 3,334,629 | A | 8/1967 | Cohn |
| 3,540,431 | A | 11/1970 | Mobin-Uddin |
| 3,868,956 | A | 3/1975 | Alfidi et al. |
| 3,952,747 | A | 4/1976 | Kimmell, Jr. |
| 4,425,908 | A | 1/1984 | Simon |

(Continued)

FOREIGN PATENT DOCUMENTS

| EP | 0 565 395 A1 | 10/1993 |
| EP | 0 809 981 A1 | 12/1997 |

(Continued)

OTHER PUBLICATIONS

International Preliminary Report on Patentability for International Application No. PCT/US06/012453 dated Oct. 18, 2007.

(Continued)

*Primary Examiner* — Darwin Erezo
*Assistant Examiner* — Amy Shipley (57) ABSTRACT A filter (10) for use within the lumen of a blood vessel that includes a plurality of interconnected intraluminal filter elements (14) adapted to flexibility convert between a filter configuration and an open configuration. The filter further includes a removable filter head (16) having a retainer (50) and a stopper (70) movable between a first position and a second position. The retainer and the stopper cooperate at the first position to secure the plurality of interconnected intraluminal filter elements into the filter configuration and the movement of the stopper to the second position releases the plurality of interconnected intraluminal filter elements to the open configuration.

14 Claims, 8 Drawing Sheets

(56) References Cited

U.S. PATENT DOCUMENTS

| | | |
|---|---|---|
| 4,494,531 A | 1/1985 | Gianturco |
| 4,643,184 A | 2/1987 | Mobin-Uddin |
| 4,657,543 A | 4/1987 | Langer et al. |
| 4,688,553 A | 8/1987 | Metals et al. |
| 4,727,873 A | 3/1988 | Mobin-Uddin |
| 4,781,177 A | 11/1988 | Lebigot et al. |
| 4,817,600 A | 4/1989 | Herms et al. |
| 4,832,055 A | 5/1989 | Palestrant |
| 4,873,978 A | 10/1989 | Ginsburg |
| 4,990,156 A | 2/1991 | Lefebvre et al. |
| 5,059,205 A | 10/1991 | El-Nounou et al. |
| 5,108,418 A | 4/1992 | Lefebvre et al. |
| 5,133,733 A | 7/1992 | Rasmussen et al. |
| 5,152,777 A | 10/1992 | Goldberg et al. |
| 5,160,342 A | 11/1992 | Reger et al. |
| 5,242,462 A | 9/1993 | El-Nounou et al. |
| 5,324,304 A | 6/1994 | Rasmussen et al. |
| 5,344,427 A | 9/1994 | Cottenceau et al. |
| 5,370,657 A | 12/1994 | Irie et al. |
| 5,375,612 A | 12/1994 | Cottenceau et al. |
| 5,383,887 A | 1/1995 | Nadal et al. |
| 5,415,630 A | 5/1995 | Gory et al. |
| 5,443,478 A | 8/1995 | Purdy |
| 5,484,424 A | 1/1996 | Cottenceau et al. |
| 5,514,154 A | 5/1996 | Lau et al. |
| 5,527,338 A | 6/1996 | Purdy |
| 5,540,680 A | 7/1996 | Guglielmi et al. |
| 5,601,595 A | 2/1997 | Smith |
| 5,618,563 A | 4/1997 | Berde et al. |
| 5,624,449 A | 4/1997 | Pham et al. |
| 5,626,605 A | 5/1997 | Irie et al. |
| 5,630,801 A | 5/1997 | Roussigne et al. |
| 5,634,942 A | 6/1997 | Chevillon et al. |
| 5,669,905 A | 9/1997 | Scheldrup et al. |
| 5,670,161 A | 9/1997 | Healy et al. |
| 5,693,067 A | 12/1997 | Purdy |
| 5,713,853 A | 2/1998 | Clark et al. |
| 5,725,550 A | 3/1998 | Nadal et al. |
| 5,743,905 A | 4/1998 | Eder et al. |
| 5,746,767 A | 5/1998 | Smith |
| 5,755,790 A | 5/1998 | Chevillon et al. |
| 5,792,400 A | 8/1998 | Talja et al. |
| 5,800,457 A | 9/1998 | Gelbfish |
| 5,810,874 A | 9/1998 | Lefebvre et al. |
| 5,836,968 A | 11/1998 | Simon et al. |
| 5,836,969 A | 11/1998 | Kim et al. |
| 5,843,118 A | 12/1998 | Sepetka et al. |
| 5,853,420 A | 12/1998 | Chevillon et al. |
| 5,893,869 A | 4/1999 | Barnhart et al. |
| 5,911,734 A | 6/1999 | Tsugita et al. |
| 6,007,558 A | 12/1999 | Ravenscroft et al. |
| 6,042,598 A | 3/2000 | Tsugita et al. |
| 6,080,178 A | 6/2000 | Meglin |
| 6,102,932 A | 8/2000 | Kurz |
| 6,214,025 B1 | 4/2001 | Thistle et al. |
| 6,241,746 B1 | 6/2001 | Bosma et al. |
| 6,241,766 B1 | 6/2001 | Liao et al. |
| 6,258,026 B1 | 7/2001 | Ravenscroft et al. |
| 6,267,776 B1 | 7/2001 | O'Connell |
| 6,306,163 B1 | 10/2001 | Fitz |
| 6,342,062 B1 | 1/2002 | Suon et al. |
| 6,342,063 B1 | 1/2002 | DeVries et al. |
| 6,391,044 B1 | 5/2002 | Yadav et al. |
| 6,447,530 B1 * | 9/2002 | Ostrovsky et al. ............ 606/200 |
| 6,517,559 B1 | 2/2003 | O'Connell |
| 6,540,767 B1 | 4/2003 | Walak et al. |
| 6,582,447 B1 | 6/2003 | Patel et al. |
| 6,702,834 B1 | 3/2004 | Boylan et al. |
| 6,972,030 B2 | 12/2005 | Lee et al. |
| 7,678,129 B1 * | 3/2010 | Gesswein et al. ............ 606/200 |
| 2003/0176888 A1 * | 9/2003 | O'Connell ................... 606/200 |
| 2003/0208253 A1 | 11/2003 | Beyer et al. |
| 2005/0015974 A1 | 1/2005 | Frutschy et al. |
| 2005/0049667 A1 * | 3/2005 | Arbefeuille et al. ......... 623/1.11 |
| 2005/0159771 A1 | 7/2005 | Petersen |
| 2006/0015137 A1 | 1/2006 | WasDyke et al. |

FOREIGN PATENT DOCUMENTS

| | | |
|---|---|---|
| EP | 1 258 228 A1 | 11/2002 |
| EP | 1 537 835 A2 | 6/2005 |
| FR | 2580504 | 10/1986 |
| FR | 2718950 | 10/1995 |
| FR | 2768326 | 3/1999 |
| WO | WO-00/49970 | 8/2000 |
| WO | WO-01/62184 A2 | 8/2001 |
| WO | WO-02/102436 A2 | 12/2002 |

OTHER PUBLICATIONS

Crochet et al., Vena Tech LGM filter: Long Term Results of a Prospective Study, Radiology, 1993, vol. 188, pp. 857 860.

Murphy et al., LGM Vena Cava Filter: Objective Evaluation of Early Results, Journal of Vascular and Interventional Radiology, 1991, vol. 2, pp. 107 115.

Taylor et al., Vena Tech Vena Cava Filter: Experience and Early Follow Up, Journal of Vascular and Interventional Radiology, 1991, vol. 2, pp. 435 440.

Cull et al., The Vena Tech Filter: Evaluation of a New Inferior Vena Cava Interruption Device, The Journal of Cardiovascular Surgery, 1991, vols. 32 50, pp. 691 696.

Ricco et al., Percutaneous Transvenous Caval Interruption with the "LGM" Filter: Early Results of a Multicenter Trial, Annals of Vascular Surgery, 1988, vol. 3, 242 247.

Mohan et al., Comparative Efficacy and Complications of Vena Caval Filters, Journal of Vascular Surgery, 1995, vol. 21 20, pp. 235 246.

Ricco et al., The LGM Vena Tech Caval Filter: Results of a Multicenter Study, Annals of Vascular Surgery, 1995, vol. 59, pp. 89 100.

Grassi et al., Vena Caval Occlusion After Simon Nitonol Filter Placement: Identification with MR Imaging in Patients with Malignancy, JVIR, 1992, vol. 3, pp. 535 539.

Johnson et al., CT of Greenfield Filters, 16th Annual Meeting SCVIR, 1991, pp. 167.

Sweeny et al., Deployment Problems with the Titanium Greenfield Filter, JVIR, 1993, vol. 4, pp. 691 694.

Milward et al., LGM (Vena Tech) Vena Caval Filter: Experiente at a Single Institution, JVIR, 1994, vol. 5, pp. 351 356.

Roehm et al., The Bird's Nest Inferior Vena Cava Filter: Progress Report, Radiology, 1988, vol. 168, pp. 745 749.

B. Braun Medical, Vena Tech Division, A Patient's Guide to the Vena Tech LGM Vena Cava Filter.

Coleman, Overview of Interruption of the Inferior Vena Cava, Seminars in Interventional Radiology, Sep. 1996, vol. 3, pp. 175 187.

Kraimps et al., Optimal Central Trapping (Opcetra) Vena Caval Filter: Results of Experimental Studies, JVIR, Nov. 1992, pp. 697 701.

Kraimps et al., Conical Endocaval Filters with Metallic Struts: Search for a New Model, Annals of Vascular Surgery, 1992, vol. 6, pp. 99 110.

Crochet et al., Caval Incorporation of the LGM Vena Tech Filter: An Experimental Study, JVIR, May Jun. 1997, pp. 419, 425.

Simon et al., Simon Nitonol Inferior Vena Cava Filter: Initial Clinical Experience, Radiology, vol. 172, pp. 99 103.

Grassi, Inferior Vena Caval Filters: Analysis of Five Currently Available Devices, AJR, Apr. 1991, vol. 156, pp. 813 821.

Dorfman, Percutaneous Inferior Vena Caval Filters, Radiology, 1990, vol. 174, pp. 987 992.

Greenfield et al., Results of a Multicenter Study of the Modified Hook Titanium Greenfield Filter, Journal of Vascular Surgery, 1991, vol. 14, pp. 253 257.

Greenfield et al., Twelve Year Clinical Experience with the Greenfield Vena Caval Filter, Surgery, Oct. 1988, pp. 706 712.

Wang et al., Use of a Nitinol Gooseneck Snare to Open an Incompletely Expanded Over the Wire Stainless Steel Greenfield Filter, AJR, Feb. 1999, vol. 172, pp. 499 500.

* cited by examiner

FIG. 8

REMOVEABLE FILTER HEAD

CROSS-REFERENCE TO RELATED APPLICATIONS

This patent claims benefit under 35 U.S.C. §119(e) to U.S. Provisional Patent Application Ser. No. 60/668,036 filed Apr. 4, 2005, the disclosure of which is hereby expressly incorporated herein by reference.

TECHNICAL FIELD

This patent generally relates to filters for use in the treatment of vascular diseases, and more specifically to filters that include a removable filter head adapted to convert, in vivo, the filter from a filter configuration to an open, stent-like configuration.

BACKGROUND

Convertible filters for treating vascular disease are known from the present inventor's own U.S. Pat. Nos. 6,267,776 and 6,517,559, the disclosures of which are hereby expressly incorporated herein by reference. These patents disclose numerous embodiments of convertible filters and particularly convertible filters suitable for treatment of vascular disease such as atherosclerotic and embolismic disease.

Generally, convertible filters include a filter structure having a plurality of filter legs arranged to form a single or double cone filter basket within the vessel lumen to trap blood borne clots or plaque with the vessel. A release member releasably secures the legs or filtering elements of the filter structure such that the filter may have two distinct configurations: filter or open/stent-like. The conversion is affected by release of the release member from the filter legs allowing the spring action of the filter legs themselves or of an externally applied opening force, such the force of a spring coupled to the filter legs, to open the filter legs from the filter configuration to the stent-like configuration. The release member may be a biodegradable material that deteriorates over time to release the filter legs to move to the stent-like configuration.

In another convertible filter, the release member is a mechanical retainer that includes a hook or similar grasping structure to allow the release member to be physically separated from the filter structure. Removal of the release member involves engaging the grasping structure with a snare and forcing the separation of the release member from the filter structure. The filter structure, which is typically attached to the wall by endothelial tissue, resists the applied force. The release member needs to be releasable from the filter legs with a minimum of force so that the reaction force exerted by the filter legs on the vessel wall does cause detrimental damage to the integrity of the wall. A well-designed release member will facilitate release of the member from the filter legs without transferring significant forces through the filter structure into the vessel wall.

Upon separation of the release member from the filter legs, the filter structure opens to assume the stent-like configuration along the wall of the blood vessel.

BRIEF DESCRIPTION OF THE DRAWINGS

For a more complete understanding of the invention, reference should be made to the following detailed description and accompanying drawings wherein.

DETAILED DESCRIPTION

The removable filter head including a release mechanism constructed in accordance with the teachings of the present invention provides a safe system for converting, in vivo, a convertible filter, such as a vena cava filter, from a closed, filter configuration to an open, stent-like configuration.

The removable filter head incorporates the release mechanism to releasably secure a plurality of interconnected intraluminal filter elements (filter elements) in a single or double cone filter structure or filter basket. The release mechanism includes a retainer adapted to receive the plurality of filter elements and a stopper movable, relative to the removable filter head and the retainer, between a secured position and an unsecured position. In operation, the filter elements are positioned within the retainer and held in position by, for example, the friction between the retainer, the filter elements and the stopper, when the stopper is in the secured position.

Movement of the stopper, relative to the removable filter head and the retainer, from the secured position adjacent to the retainer to the unsecured position, releases the filter elements while maintaining the position of the removable filter head relative to the filter elements and the wall of the blood vessel. Subsequently, the released filter elements can convert or expand from the filter configuration to the stent-like configuration when the removable filter head is physically separated from the filter elements.

Figure 1:
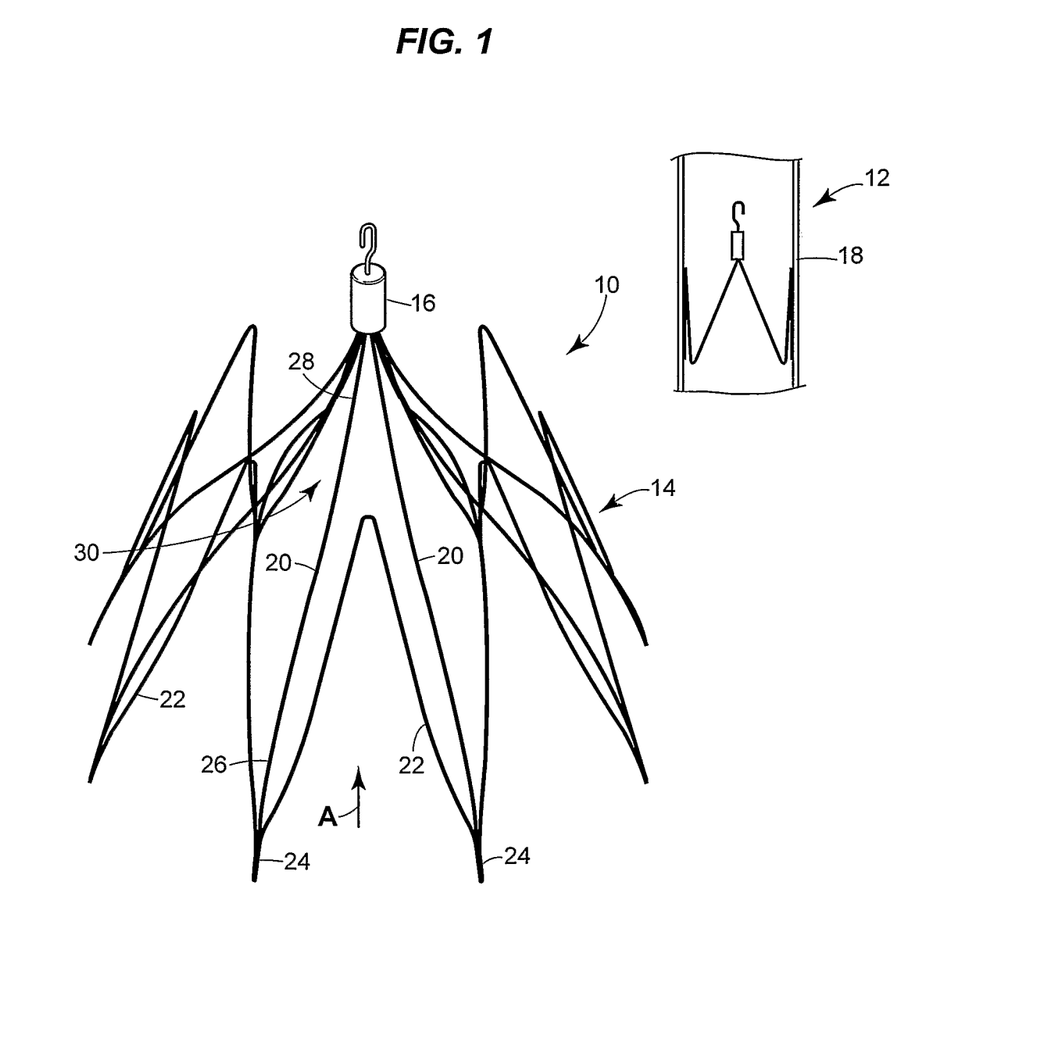
FIG. 1 illustrates a side view of an exemplary convertible filter assembly constructed in accordance with the teachings of the present invention.
Figure 2:
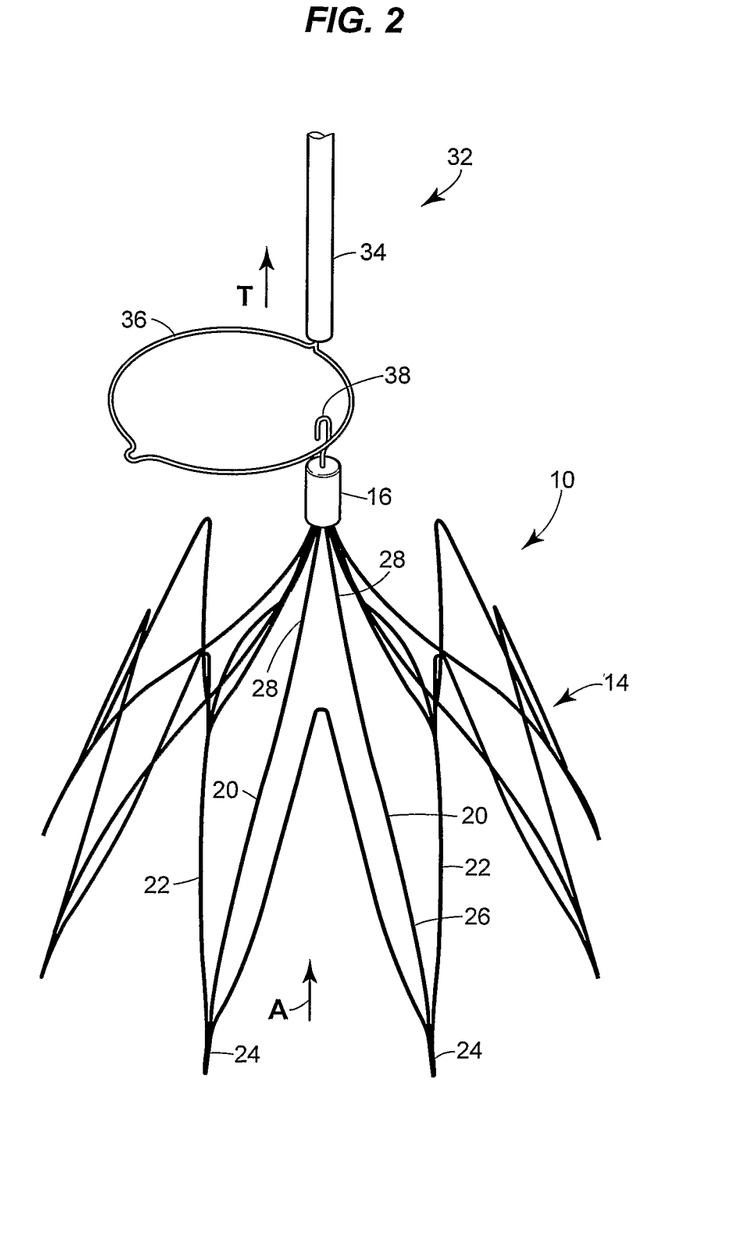
FIG. 2 illustrates the convertible filter assembly of FIG. 1 aligned with a grasping device.
Figure 3:
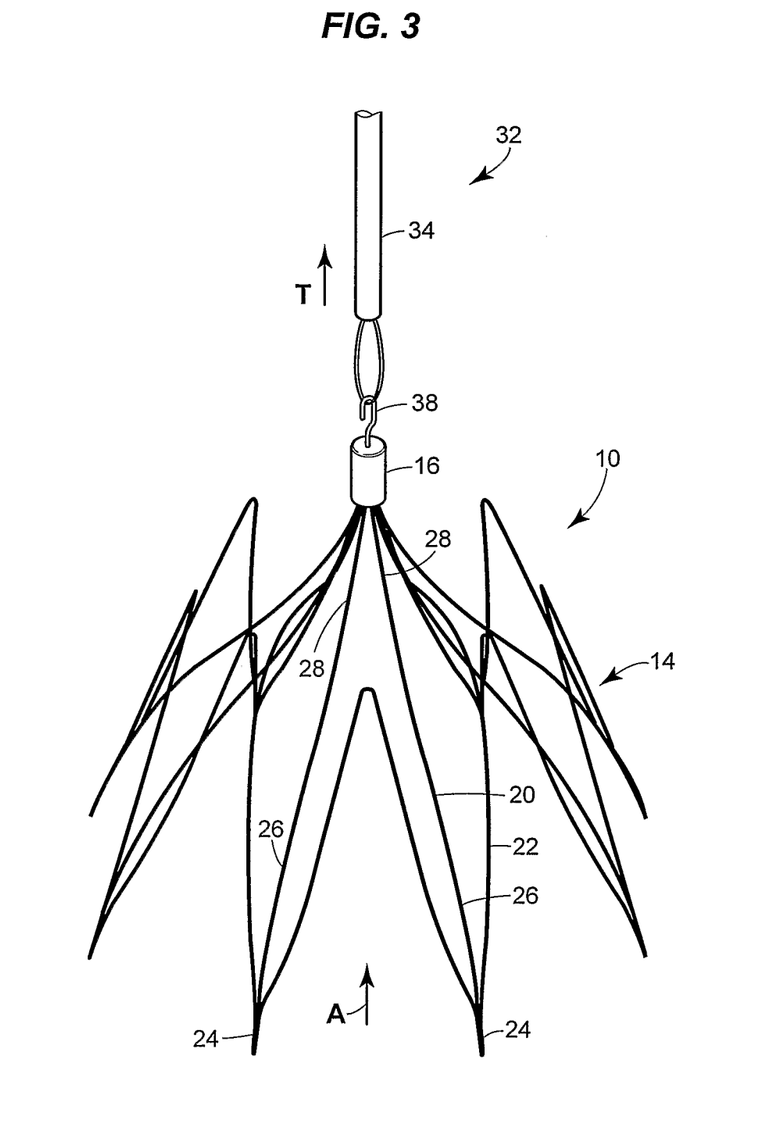
FIG. 3 illustrates an enlarged view of a removable filter head portion of the convertible filter assembly cooperating with the grasping device in a retracted state.

FIGS. 1-3 generally illustrate a convertible filter assembly 10 deployed in a filter configuration within the lumen of a blood vessel 12. The convertible filter assembly 10 includes a plurality of intraluminal filter elements (filter elements) 14 secured in the filter configuration by a removable filter head 16, as shown in FIG. 1. The term "filter configuration" as used herein refers to the convertible filter assembly 10 when positioned within the blood vessel 12 for the treatment of vascular diseases. Similarly, the terms "open configuration" or "stent-like configuration" refer to the convertible filter assembly 10 with the removable filter head 16 separated from the filter elements 14, and the unrestrained filter elements 14 extended along a wall 18 of the blood vessel 12.

The filter elements 14 in this exemplary embodiment are arranged in a single cone configuration and aligned within the blood vessel 12 in the direction of the blood flow indicated by the arrow A to trap matter carried within the blood flow, for example, dislodged blood clots or plaque. The filter elements 14 each include a filter leg 20 flexibly attached to an orientation member 22 at a flexure point 24. In operation, deployment of the convertible filter assembly 10 within the blood vessel 12 allows the orientation members 22 to engage the wall 18 of the blood vessel 12 and align the entire convertible filter assembly 10 with the blood flow. However, it is noted that the particular configuration of the convertible filter, single cone, dual cone, basket, stabilizing members or no stabilizing members, etc., is not critical, and the herein described removable filter head is adaptable to virtually any such structure.

The filter legs 20 include an inferior end 26 and a superior end 28 aligned along the wall 18 of the blood vessel 12 by the orientation member 22. In particular, the inferior end 26 is an unsecured portion of the filter leg 20 positioned upstream from the superior end 28. The superior end 28 is, in turn, bundled and secured together by the removable filter head 16 to form a filter basket generally indicated by the reference numeral 30. As used herein to assist the reader, the terms superior and inferior indicate the orientation of the convertible filter assembly 10 within the blood vessel 12 and relative to the direction of the blood flow (indicated by the arrow A). For example, the term inferior indicates a downstream position and the term superior indicates an upstream position relative to the direction of blood flow within the blood vessel 12.

The convertible filter assembly 10 including the removable filter head 16, the filter legs 20 and the orientation members 22 may be manufactured from a radiopaque and non-ferromagnetic metal that has been certified for use in medical devices by the International Standards Organization (ISO). The filter legs 20 and the orientation members 22 may be manufactured from metallic wires having, for example, a round, flat or any suitable cross-sectional shape. The convertible filter assembly 10 may be further drug-coated.

The wires may be a high cobalt, low ferrous alloy, such as the alloys sold under the registered trademark ELGILOY® which is also referred to as PHYNOX. The composition of these alloys may, by weight percent, be: cobalt 42%, chromium 21.5%, nickel 18%, iron 8.85%, molybdenum 7.5%, manganese 2% with the balance made up of carbon and beryllium having a maximum of 0.15% carbon and 0.001% beryllium. The wires may also be composed of 316L stainless steel or other alloys of nickel and titanium known to be shape-memory metals which are sold and manufactured under the registered trademark NITINOL® or an alloy of tantalum (Ta). Convertible filter assemblies 10 constructed from these metals will be non-thrombogenic and preferably withstand twelve million respiratory cycles without mechanical failure.

FIGS. 2 and 3 generally illustrate the convertible filter assembly 10 deployed within the blood vessel 12 and aligned with a snare catheter 32. In particular, FIGS. 2 and 3 illustrate the alignment and capture of the removable filter head 16 by the snare catheter 32. The snare catheter 32, or any other suitable gripping device, can be inserted into the lumen of the blood vessel by any known method of insertion and deployment, and maneuvered through the patient's circulatory system to a position adjacent to the removable filter head 16 and the superior end 28 of the filter legs 20. The snare catheter 32 may include a sheath 34 and a snare 36 such as, for example, a gooseneck snare or a hook, slideable relative to the sheath 34. Similarly, the removable filter head 16 may include a catch 38 or hook adapted to be engaged by the snare 36.

FIG. 3 illustrates an enlarged view the removable filter head 16 deployed within the blood vessel 12 and engaged by the snare catheter 32. In particular, FIG. 3 shows the snare catheter 32 maneuvered, via a patient's circulatory or cardiovascular system, to a position adjacent to the removable filer head 16. From this position, the snare 36 can loop around or otherwise grasp the catch 38 to slideably secure the snare catheter 32 and sheath 34 to the removable filter head 16. By increasing the tension in the direction indicated by the arrow T, the snare 36 can be retracted into the sheath 34 while simultaneously sliding the sheath 34 towards the removable filter head 16. It will be understood that the applied tension T will be sufficient to withdraw the snare 36 into the sheath 24, but not great enough to shift or disturb the overall position of the convertible filter assembly 10 relative to the wall 18 of the blood vessel wall 12.

Figures 4, 5:
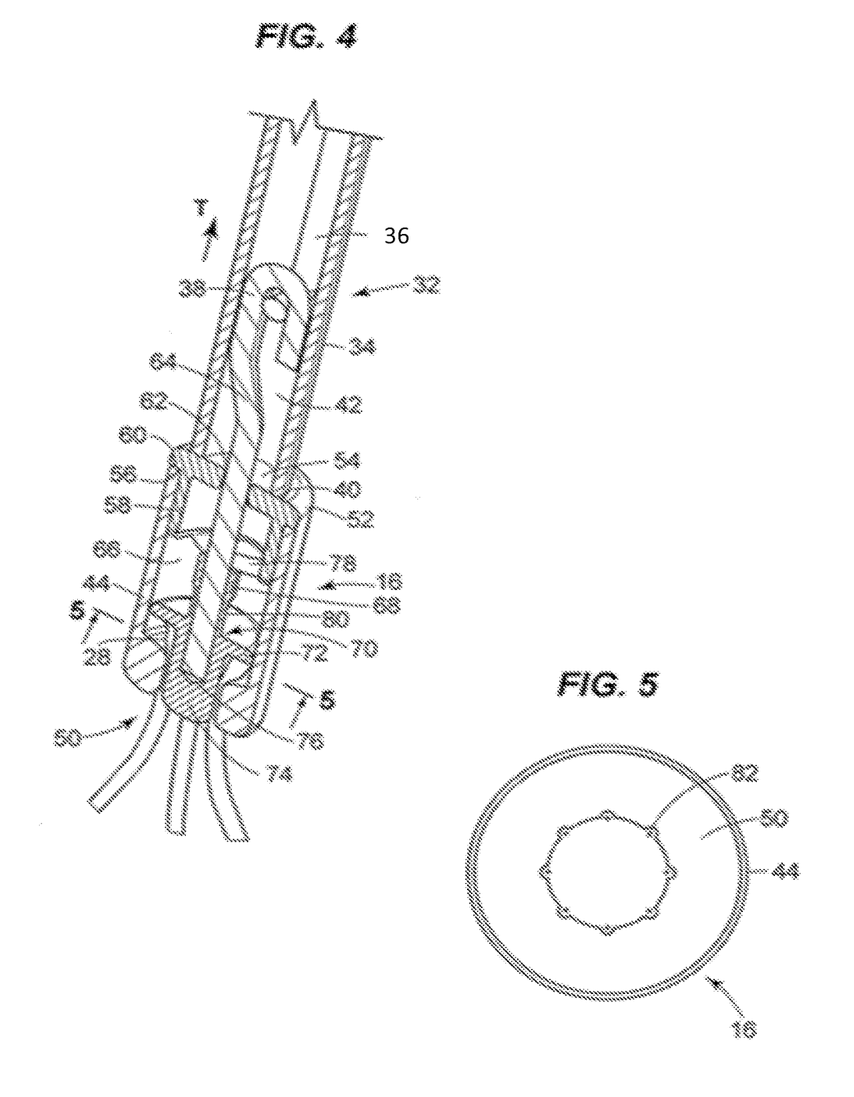
FIG. 4 illustrates an enlarged cross-sectional view of the removable filter head and grasping device of FIG. 3.
FIG. 5 illustrates a cross-sectional view of the removable filter head taken along the line 5-5.

FIG. 4 illustrates an enlarged cross-sectional view of the snare catheter 32 in an abutting relationship with removable filter head 16. Specifically, the snare catheter 32 includes a tip 40, defined as the terminal end of the sheath 34, in an abutting relationship with the removable filter head 16. As shown, the tip 40 is firmly seated against the removable filter head 16 and the snare 36 and catch 38 are retracted into the hollow interior 42.

The removable filter head 16 is a roughly cylindrical body 44 that includes an open first end 46 and a second end 48 that includes a retainer 50 formed integrally therein. The open first end 46 accepts an end cap 52 sized to close and/or seal the roughly cylindrical body 44. The end cap 52 includes a lip 56 which can be seated against a top edge 60 of the cylindrical body 44, and a cylindrical wall 58 sized to cooperate with the interior surface of the cylindrical body 44 such that the lip 56 and a top edge 60 of the cylindrical body 44 are in an abutting relationship. The cylindrical wall 58 and the cylindrical body 44 may be held together in a press-fit or friction arrangement, may include male and female threads and be rotatably joined and may be glued, welded or otherwise secured together in any desired manner. The end cap may further include an external, flat surface 54 arranged to bear against and/or bias the tip 40 of the sheath 34 when the snare 36 and catch 38 are retracted into the hollow interior 42. The flat surface 54 provides a firm contact between the two components, the removable filter head 16 and the snare catheter 32, and allows the transmission of forces therebetween.

The end cap 52 further includes an orifice 62 sized to slideably accept a rod portion 64 connected to the catch 38. The rod portion 64 extends through the orifice 62 into an interior 66 of the cylindrical body 44 to engage a stopper 70 having a contiguously formed shaft 68. The stopper 70, as shown in this exemplary embodiment, is a roughly cylindrical component sized to releasably engage the retainer 50 formed at the second end 48 of the cylindrical body 44. In operation, the stopper 70 is movable within the interior 66 of the cylindrical body 44 between a secured position adjacent to the retainer 50, and an unsecured position adjacent to the end cap 54.

The stopper 70 includes varying diameter portions that define a flange 72 and plug 74. The flange 72 and plug 74, of this present embodiment, are integral elements which are aligned coaxially with the shaft 68 and the rod portion 64. Physically, the flange 72 is a radially extending disc that compliments the interior 66 of the cylindrical body 44 and the plug 74 has a reduced diameter, relative to the flange 72, sized to cooperate with the retainer 50 when the stopper 70 is in the secured position. The, shaft 68, as shown, may includes a blind bore 76 sized to securely accept the rod portion 64 in, for example, a threaded or press fit arrangement. The removable filter head 16 may further include a push nut 78 positioned adjacent to the cylindrical wall 58 of the end cap 52 to hold the stopper 70, via the shaft 68 and flange 72, in secure contact with the retainer 50.

A force applied through the catch 38 and rod portion 62 in the direction indicated by the arrow T allows the shaft 68 to elastically deform the push nut 78 and move the stopper 70 to the unsecured position adjacent 48 to the cylindrical wall 58 of the end cap 52. The cylindrical wall 58 and push nut 78 cooperate with the flange 72 to limit the overall movement of the stopper 70 to the unsecured position adjacent to the end cap 52. The shaft 68 further includes a reduced diameter portion 80 adjacent to the flange 72 and arranged to cooperate with the push nut 78 to, upon movement to the unsecured position at the open first end 46, prevent the stopper 70 and plug from reengaging the retainer 50.

The plug 74 and the retainer 50 cooperate to compressively engage and retain the superior ends 28 of the filter legs 20 when the stopper 70 is in the secured position. The superior end 28 of the filter legs 20 may be aligned within a plurality of grooves 82 (see FIG. 5) formed within the retainer 50 at the second end 48 of the cylindrical body 44. The aligned filter legs 20 may, in turn, be held in position by inserting the plug 74 into the retainer 50 and creating an interference fit therebetween. Moreover, the flange 72 may be sized and arranged to compressively engage the aligned superior ends of the filter legs 20 against the retainer 50. In this way, the superior ends 28 of the filter legs 20 are aligned and secured within the cylindrical body 44 of the removable filter head 16 to thereby create the filter basket 30.

Figure 6:
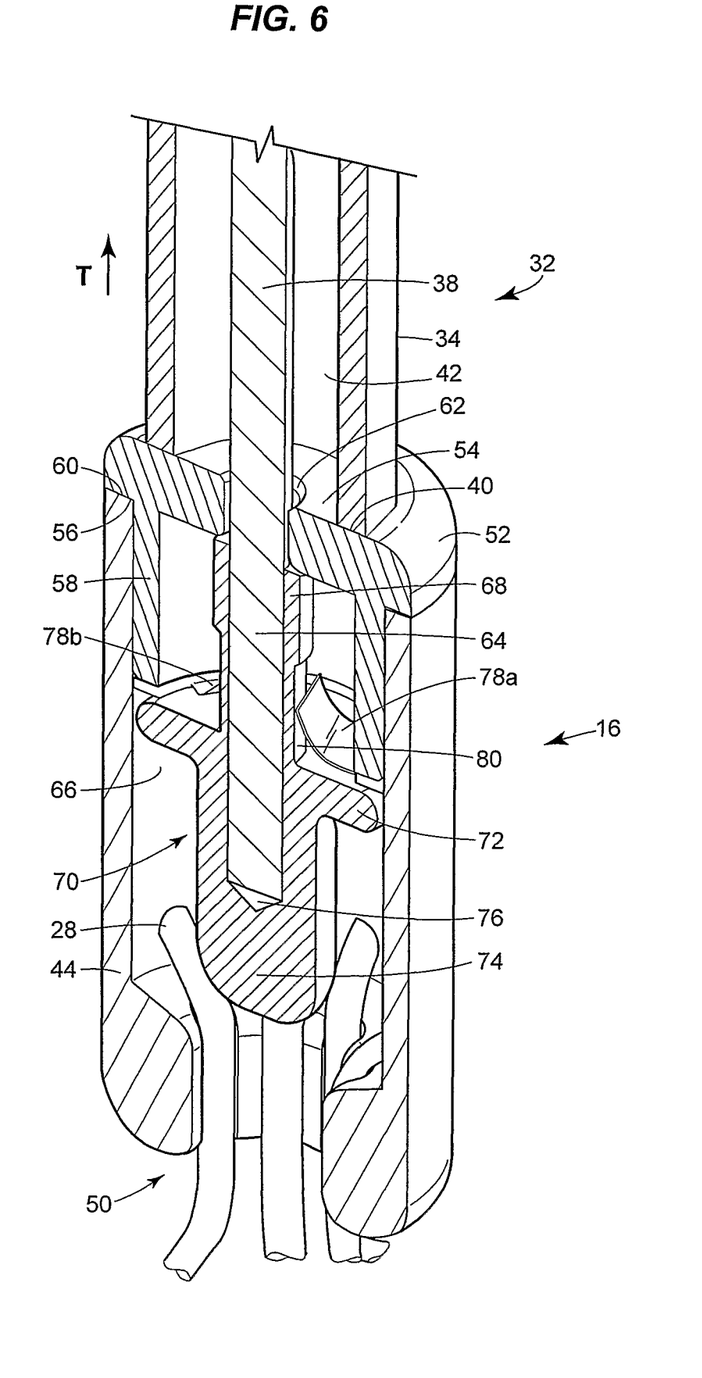
FIG. 6 illustrates the enlarged cross-sectional view of the removable filter head and grasping device of FIG. 4 shown in an unsecured position.

FIG. 6 illustrates an enlarged cross-sectional view of the removable filter head 16 in an abutting relationship with the tip 40 of the snare catheter 32. In particular, the catch 38 and the snare 36 are withdrawn into the sheath 34 such that the tip 40 is firmly seated against the flat surface 54. Moreover, the application of tension through the snare 36 and the catch 38, in the direction indicated by the arrow T, forces the stopper 70 to move towards the unsecured position adjacent to the end cap 52.

The movement of the stopper 70, in turn, causes the shaft 68 to bear against and elastically deform the push nut 78. In particular, the stopper movement elastically deforms the fingers, indicated by the numerals 78a and 78b, of the push nut 78. The elastically deformed fingers 78a, 78b ride along the shaft 68 and engage a reduced diameter portion 80 to prevent the stopper 70 from returning to the secured position adjacent to the retainer 50. Similarly, the flange 72 engages the cylindrical wall 58 and prevents additional movement or overtravel in the direction of the end cap 52. In this way, the stopper 70 is locked into the unsecured position away from the retainer 50 and between the end cap 52 and the retainer 50. The reduced diameter portion 80 may further act as a detent such that as the stopper 70 arrives at the unsecured position, it is engaged by the reduced diameter portion to retain it in the unsecured position. The action of the fingers sliding from the shaft 68 to the reduced diameter portion may also provide a haptic snap or click indication through the catheter, allowing the medical professional to know that the stopper 70 is fully retracted to the unsecured position.

The tension applied to retract the stopper 70 and elastically deform the push nut 78, can cause the entire convertible filter assembly 10 to move in order to react forces against the blood vessel wall 18. In order to limit force transfer to the vessel wall, the tension applied through the snare 36 is counteracted and balanced by an equal and opposite force applied to the flat surface 54 through the sheath 34. In this way, while the catch 38 and the attached stopper 70 are forced to disengage from the retainer 50, the counterforce applied through the sheath 34 maintains the position of the removable filter head 16 and attached filter elements 14, relative to the blood vessel wall 18.

As shown in FIG. 6, upon disengagement of the plug 74 from the retainer 50, the stopper 70 remains secured adjacent to the end cap 52 by the cooperation of the reduced diameter portion 80 and the fingers 78a, 78b of the push nut 78. The superior ends 28 of the filter legs 20 will typically remain aligned within the grooves 82 of the retainer 50, but will be unfettered and ready for release. This arrangement allows convertible filter assembly 10 to be transitioned from the filter configuration to the open or stent-like configuration by releasing the superior ends 28 of the filter legs 20 from the retainer 50.

As outlined above, the process of transitioning the convertible filter assembly 10 begins with maneuvering and aligning the snare catheter 32 and the snare 36 with the removable filter head 16 and the catch 38. The aligned snare 36 engages the catch 38, and the sheath 34 is positioned in contact with the flat surface 54 of the end cap 52. In this way, the tip 40 of the snare catheter 32 abuts the removable filter head 16 (through contact with the end cap 52) and the sheath 34 encloses both the snare 36 and the catch 38.

Application of tension in the direction of the arrow T to the free end of the snare 36, e.g., the end of the snare 36 which is outside of the patient's body, pulls the catch 38 deeper into the sheath 34 and forces the attached stopper 70 to disengage from the retainer 50. It will be understood that unless the tension is greater than the force generated by the fingers 78a, 78b of the push nut 78 and the friction between the plug 74 and the retainer 50, the stopper 70 cannot be disengaged. Simultaneously, a counterforce can be applied to the removable filter head 16 through the sheath 34 in order to balance and counteract the effects of the tension applied through the snare 36. In other words, as the snare 36 is pulled to release the plug 74 from the retainer 50, the sheath 34 is pushed to engage the removable filter head 16 through the flat surface 54 of the end cap 52 and prevent movement relative to the blood vessel wall 18.

By overcoming the friction between the plug 74 and the retainer 50, the shaft 68 elastically deforms the fingers 78a, 78b of the push nut 78 and allows the stopper 70 to move away from the retainer 70 and to the unsecured position adjacent to the end cap 52. The fingers 78a, 78b, in turn, engage the reduced diameter portion 80 and lock or otherwise prevent the stopper 70 from reengaging the retainer 50. The movement of the stopper 70 is further limited, by the interference between the flange 72 and the cylindrical wall 58 of the end cap 52. This release mechanism within the removable filter head 16 allows the stopper 70 to be disengaged from the retainer 50 and prevents unwanted reengagement of the components.

Figure 7:
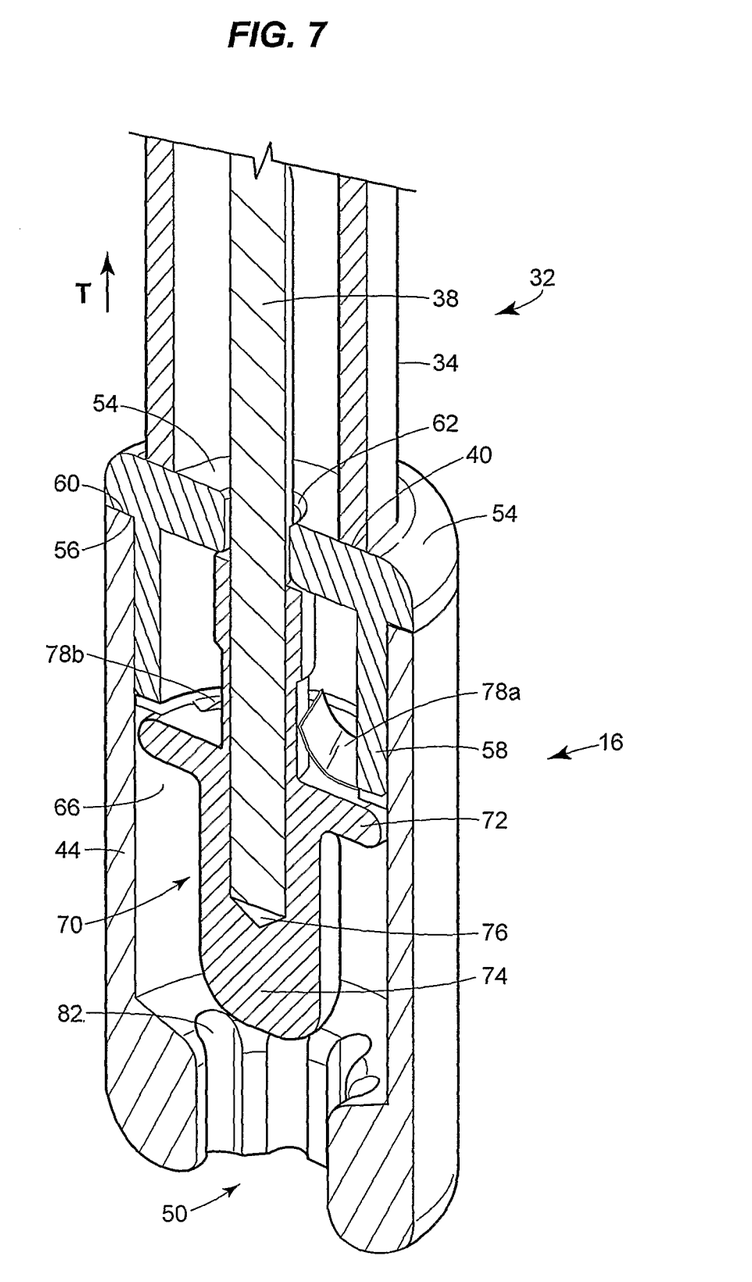
FIG. 7 illustrates the enlarged cross-sectional view of the removable filter head and grasping device of FIG. 6 after the release of the unsecured filter elements.

FIG. 7 illustrates the removable filter head 16 after the stopper 70 and plug 74 have been disengaged from the retainer 50. The unrestrained superior ends 28 of the filter legs 20 have been released from the grooves 82, and have flexed or expanded to the open or stent-like configuration. Generally, in order to disengage the removable filter head 16 and release the superior ends 28 of the filter legs 20, the entire removable filter head 16 is pulled, via the snare catheter 32, away from the filter elements 14 lodged or encapsulated in the wall 18 of the blood vessel 12. In this way, the removable filter head 16 and the snare catheter 32 are separated from the filter elements 14 for extraction through the patient's circulatory system. The filter elements 14 remain secured to the wall 18 of the blood vessel 12 in the open or stent-like configuration.

Figure 7A:
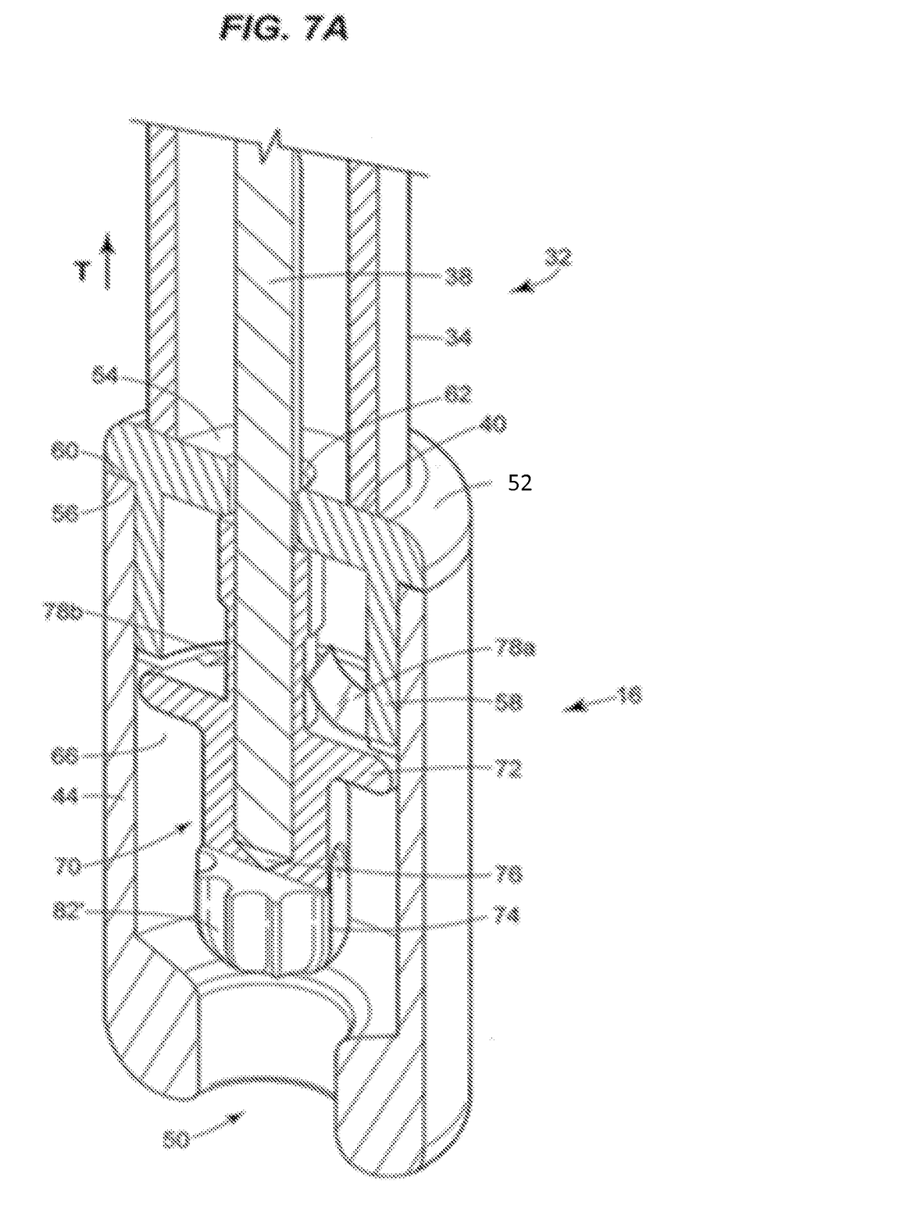
FIG. 7a illustrates the enlarged cross-sectional view of an alternative construction of the removable filter head and grasping device of FIG. 6 after the release of the unsecured filter elements.

FIG. 7a illustrates an alternative construction of the removable filter head 16 after the stopper and plug 74 have been disengaged from the retainer 50. Like reference numerals designate like elements. The retainer 50 is formed with a smooth bore that receives the superior ends 28 of the filter legs. The stopper and plug 74 are formed with grooves 82' that engage and align the filter legs with the stopper and plug 74 in the secured position, and, as shown in FIG. 7a, release the filter legs when in an unsecured position. Alternative arrangements wherein grooves 82/82' are formed in one or both of the retainer 50 or plug 74 may be used.

Figure 8:
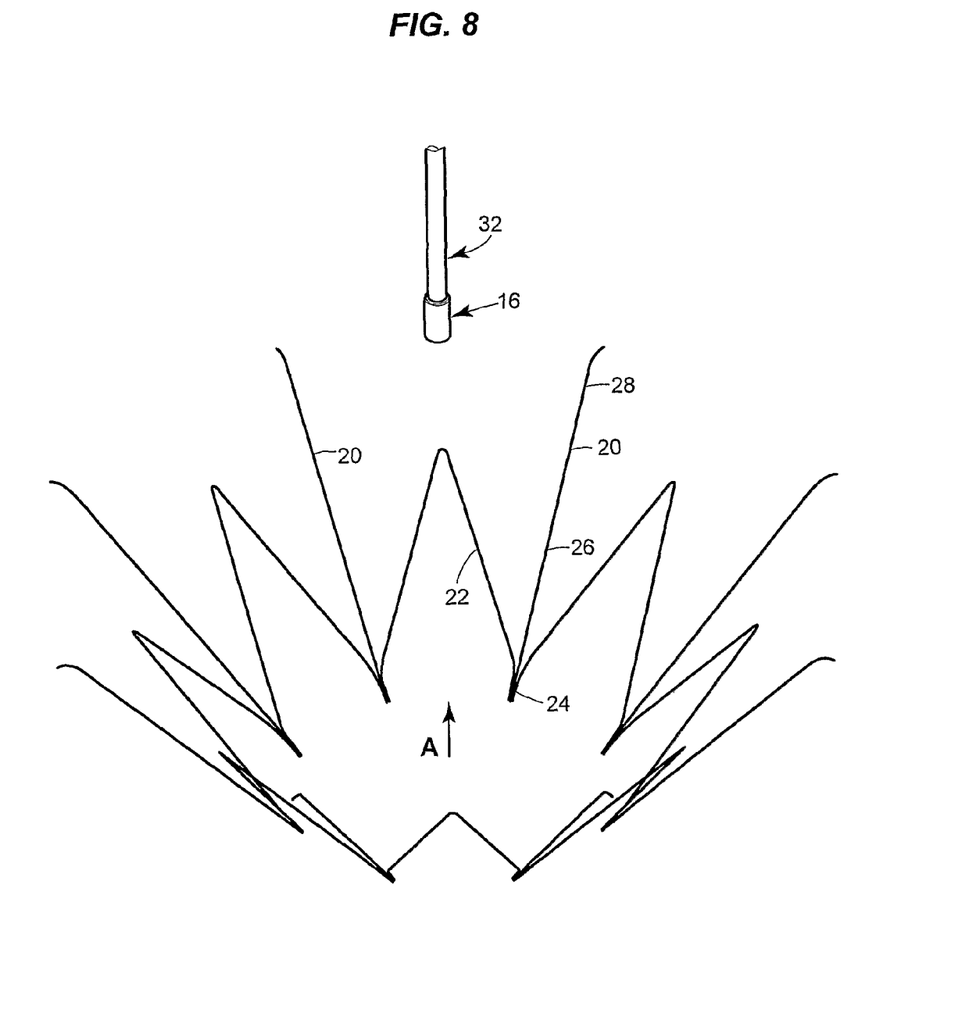
FIG. 8 illustrates a perspective view of the convertible filter assembly after separation of the removable filter head.

FIG. 8 illustrates the released intraluminal filter elements 14 expanded and extended along the wall 18 of the blood vessel 12. In this open or stent-like configuration, the filter basket 30 is open and allows blood to flow freely through the blood vessel 12.

Although certain embodiments have been described in accordance with the teachings of the present disclosure, the scope and coverage of this patent is not limited thereto. For instance, while the removable filter 14 has been illustrated and describes as having a cylindrical body, it will be understood that any desired shape or configuration may be employed. Further, while a specific embodiment of the intraluminal filter elements 14 has been described herein, many other single or double cone arrangements may be employed. This patent is intended to cover all embodiments of the teachings of the disclosure that fairly fall within the scope of the permissible equivalents.

What is claimed is:

1. A filter for use within the lumen of a blood vessel that includes a plurality of interconnected intraluminal filter elements adapted to flexibly convert between a filter configuration and an open configuration, the filter comprising: a removable filter head including, a retainer; and a stopper movable between a first position and a second position relative to the removable filter head and the retainer; wherein the retainer and the stopper cooperate at the first position to secure the plurality of interconnected intraluminal filter elements into the filter configuration and wherein the movement of the stopper to the second position releases the plurality of interconnected intraluminal filter elements to the open configuration; and a catch fixedly attached to the stopper and adapted to mechanically release the stopper from the retainer in response a releasing force, wherein the releasing force is provided by a snare catheter positioned adjacent to the catch and the removable filter head.

2. The filter of claim 1, wherein the catch is a hook adapted to cooperate with a snare portion of the snare catheter to mechanically release the stopper from the retainer.

3. The filter of claim 1, wherein the removable filter head includes a push nut arranged to limit the travel of the stopper relative to the retainer.

4. The filter of claim 3, wherein the push nut includes a plurality of elastically deformable fingers adapted to secure the stopper in the second position.

5. The filter of claim 1, wherein the retainer includes a plurality of grooves adapted to receive the plurality of interconnected intraluminal filter elements.

6. A removable filter head adapted to secure a plurality of interconnected intraluminal filter elements in a filter configuration, the removable filter head comprising: a retainer sized to accept the plurality of interconnected intraluminal filter elements; and a stopper movable between a first position and a second position relative to the retainer, wherein the stopper is sized to engage the plurality of interconnected intraluminal filter elements and the retainer, and wherein the movement of the stopper from the first position to the second position releases the plurality of interconnected intraluminal filter elements and the retainer is formed within a cylindrical body having an integral side wall, an open end to receive the intraluminal filter elements and an enclosed end formed with an aperture through which a rod portion of the stopper extends, further comprising a catch fixedly attached to the stopper and arranged to move the stopper from the first position to the second position in response to a releasing force.

7. The removable filter head of claim 6, further comprising a flat surface arranged to bias the releasing force and prevent movement of the retainer relative to the plurality of interconnected intraluminal filter elements.

8. The removable filter head of claim 7, wherein the releasing force is transmitted by a catheter having a snare, and wherein the catheter is arranged to abut the flat surface and the snare is arranged to engage the catch.

9. The removable filter head of claim 6, wherein the catch is a hook fixedly attached the stopper and sized to cooperate with a snare catheter to move the stopper to the second position.

10. The removable filter head of claim 6, wherein the retainer body includes a push nut arranged to limit the movement of the stopper.

11. The removable filter head of claim 6, wherein the stopper includes a flange sized to compressively engage the plurality of interconnected intraluminal filter elements.

12. A method of converting a filter including a plurality of interconnected intraluminal filter elements positioned within the lumen of a blood vessel to an open configuration, the method comprising: inserting a snare catheter having a first end into the lumen of the blood vessel; positioning the snare catheter adjacent to a removable filter head having a retainer and a release mechanism, wherein the release mechanism is adapted to releasably secure the plurality of interconnected intraluminal filter elements; engaging the release mechanism with snare catheter; shifting the release mechanism relative to the removable filter head and the retainer to thereby release the plurality of interconnected intraluminal filter elements.

13. A filter for use within the lumen of a blood vessel that includes a plurality of interconnected intraluminal filter elements adapted to flexibly convert between a filter configuration and an open configuration, the filter comprising: a removable filter head including, a retainer; and a stopper movable between a first position and a second position relative to the removable filter head and the retainer; wherein the retainer and the stopper cooperate at the first position to secure the plurality of interconnected intraluminal filter elements into the filter configuration and wherein the movement of the stopper to the second position releases the plurality of interconnected intraluminal filter elements to the open configuration; and the removable filter head includes a push nut arranged to limit the travel of the stopper relative to the retainer.

14. The filter of claim 13, wherein the push nut includes a plurality of elastically deformable fingers adapted to secure the stopper in the second position.

* * * * *